US012653620B2

(12) United States Patent
Black

(10) Patent No.: US 12,653,620 B2
(45) Date of Patent: Jun. 16, 2026

(54) AUTOMATIC SEGMENTATION AND REGISTRATION SYSTEM AND METHOD

(71) Applicant: MEDIVIEW XR, INC., Cleveland, OH (US)

(72) Inventor: John Black, Bowling Green, OH (US)

(73) Assignee: MEDIVIEW XR, INC., Cleveland, OH (US)

( * ) Notice: Subject to any disclaimer, the term of this patent is extended or adjusted under 35 U.S.C. 154(b) by 1185 days.

(21) Appl. No.: 17/505,772

(22) Filed: Oct. 20, 2021

(65) Prior Publication Data

US 2022/0117674 A1 Apr. 21, 2022

Related U.S. Application Data

(60) Provisional application No. 63/093,904, filed on Oct. 20, 2020.

(51) Int. Cl.
*A61B 34/20* (2016.01)
*A61B 5/00* (2006.01)
(Continued)

(52) U.S. Cl.
CPC .............. *A61B 34/20* (2016.02); *A61B 5/745* (2013.01); *A61B 8/46* (2013.01); *G06F 18/251* (2023.01); *G06N 20/00* (2019.01); *G06T 19/006* (2013.01); *A61B 2034/105* (2016.02); *A61B 2034/2055* (2016.02)

(58) Field of Classification Search
None
See application file for complete search history.

(56) References Cited

U.S. PATENT DOCUMENTS 6,690,960 B2 * 2/2004 Chen ...................... A61B 34/20
600/407
10,743,941 B2 8/2020 Vanderbilt
(Continued)

FOREIGN PATENT DOCUMENTS

CN 111798498 A 10/2020
JP 2018514340 A 6/2018
(Continued)

OTHER PUBLICATIONS

Written Opinion of the International Searching Authority dated Jan. 21, 2022.

*Primary Examiner* — Jason A Pringle-Parker
(74) *Attorney, Agent, or Firm* — Jacob M. Ward; Ward Law Office LLC

(57) ABSTRACT

A holographic augmented reality visualization and guidance system for performing a medical procedure includes an augmented reality system for displaying operating information to a user. The operating information can include preoperative data, intraoperative data, and fused data of an anatomical structure. A computer system is in communication with the augmented reality system and is configured to selectively generate the fused data by merging the preoperative data and the intraoperative data, identify deformation of the anatomical structure via differences between the preoperative data and the intraoperative data, transmit the operating information to the augmented reality system, and compensate for the deformation of the anatomical structure according to the deformation engine in real-time.

8 Claims, 6 Drawing Sheets

(51) Int. Cl.

| | |
|---|---|
| *A61B 8/00* | (2006.01) |
| *A61B 34/10* | (2016.01) |
| *G06F 18/25* | (2023.01) |
| *G06N 20/00* | (2019.01) |
| *G06T 19/00* | (2011.01) |

(56) References Cited

U.S. PATENT DOCUMENTS

| | | | |
|---|---|---|---|
| 10,895,906 B2 | 1/2021 | West et al. | |
| 2010/0194863 A1 | 8/2010 | Lopes et al. | |
| 2012/0087563 A1* | 4/2012 | Ionasec | G06T 19/006 |
| | | | 382/128 |
| 2015/0146946 A1* | 5/2015 | Elhawary | G06T 19/00 |
| | | | 382/128 |
| 2016/0191887 A1* | 6/2016 | Casas | H04N 13/156 |
| | | | 348/47 |
| 2016/0302747 A1* | 10/2016 | Averbuch | A61B 6/5235 |
| 2017/0071673 A1* | 3/2017 | Ferro | A61B 5/1079 |
| 2018/0303563 A1* | 10/2018 | West | A61B 90/37 |
| 2019/0008592 A1* | 1/2019 | Thienphrapa | A61B 1/0004 |
| 2019/0015163 A1* | 1/2019 | Abhari | H04N 7/181 |
| 2019/0053855 A1* | 2/2019 | Siemionow | A61B 90/37 |
| 2020/0188028 A1* | 6/2020 | Feiner | G16H 50/50 |
| 2020/0246074 A1 | 8/2020 | Lang | |
| 2021/0161612 A1 | 6/2021 | Black et al. | |
| 2021/0169587 A1 | 6/2021 | Martin, III et al. | |

FOREIGN PATENT DOCUMENTS

| | | | |
|---|---|---|---|
| JP | 2020058779 A | 4/2020 |
| JP | 2020527087 A | 9/2020 |
| WO | 2019217795 A1 | 11/2019 |
| WO | 2020054503 A1 | 3/2020 |

* cited by examiner

104

| 121 | 119 | 117 | |
| BOTTOM PORTION 120 | MIDDLE PORTION 118 | TOP PORTION 116 | TIP PORTION 114 | 115 |

103

AUTOMATIC SEGMENTATION AND REGISTRATION SYSTEM AND METHOD

CROSS-REFERENCE TO RELATED APPLICATIONS

This application claims priority to and the benefit of U.S. Provisional Application No. 63/093,904, filed on Oct. 20, 2020. The disclosure of the above application is incorporated herein by reference.

FIELD

The present disclosure relates to augmented reality applications, and more particularly, to medical applications employing augmented reality.

INTRODUCTION

This section provides background information related to the present disclosure which is not necessarily prior art.

Image-guided surgery has become standard practice for performing different medical procedures on an anatomical site of a patient. Image-guided surgery can visually correlate intraoperative data with preoperative data to aid a user, such as a medical practitioner. The use of image-guided surgeries can increase the safety and the success of these procedures. Image-guided surgeries can be further enhanced through the use of augmented reality technology. Augmented reality can include an interactive experience of a real-world environment where one or more features that reside in the real world are enhanced by computer-generated perceptual information, sometimes across multiple sensory modalities. In the medical settings, these augmented reality technologies can be useful for enhancing the real environments in the patient care setting. For example, a user can view content-specific information in the same field of view of the patient while performing the medical procedure, without having to change their gaze.

Medical image segmentation technology can be used to support the clinical imaging workflow from diagnosis, therapy planning, intervention planning, and follow-up. Segmentation of anatomical objects or structures is necessary for many medical image tasks, such as motion tracking, diagnosis, and quantification. Medical image registration is used to detect anatomical objects or structures in different medical imaging modalities, such as computed tomography (CT), cone beam computed tomography (CBCT), magnetic resonance imaging (MRI) systems, positron emission tomography (PET), and fluoroscopic imaging.

Ultrasound systems can provide a real-time imaging component; however, the echogenicity of a structure can result in poor image quality of critical structures. In modern ultrasound imaging, clinical image quality is important for accurate diagnoses and navigation for interventional procedures. Echogenicity is the ability of a structure to bounce an echo, e.g., return a signal in ultrasound examinations. Echogenicity is higher when the surface bouncing the sound echo reflects increased sound waves. Tissues that have higher echogenicity are called "hyperechogenic" and are usually represented with lighter colors on ultrasound images. In contrast, tissues with lower echogenicity are called "hypoechogenic" and are usually represented with darker colors. Areas that lack echogenicity are called "anechogenic" and are usually displayed as completely dark. Undesirably, the echogenicity of structures can lead to poor imaging of critical structures and/or blind spots during the medical procedure. Furthermore, other factors, such as shadowing or the inability for users to obtain correct angles of the ultrasound probe due to obstructing structures, can lead to poor image quality, among other issues, during the medical procedure. One known solution is to obtain preoperative imaging from other imaging modalities. However, relying on preoperative images can result in losing the benefits of intraoperative imaging, such as ultrasound. A user can choose to use both preoperative imaging and intraoperative imaging, however shifting back and forth between different images can be difficult and time-consuming. In addition, certain anatomical structures of the body can deform or shift overtime due to a multitude of different factors. Undesirably, the intraoperative imaging can look different from the preoperative imaging due to the anatomical structures deforming or shifting after the preoperative image was captured.

There is a continuing needed for a visualization and guidance system and method for performing a medical procedure that can militate against real-time imaging limitations, such as hypoechogenic structures or obstructing structures that create shadowing or inhibits angling of the ultrasound probe. Desirably, the system and method can adjust for deformable anatomy.

SUMMARY

In concordance with the instant disclosure, systems and methods for holographic augmented reality visualization and guidance in performing a medical procedure on a patient by a user, which allow for deformation correction of segmented anatomical structures that have deformed or shifted after a preoperative image was captured, and which enhance image quality, have been surprisingly discovered.

In certain embodiments, a holographic augmented reality visualization and guidance system for performing a medical procedure includes an augmented reality system for displaying operating information to a user. The operating information can include preoperative data, intraoperative data and fused data of an anatomical structure. A computer system is in communication with the augmented reality system and is configured to selectively generate the fused data by merging the preoperative data and the intraoperative data, identify deformation of the anatomical structure via differences between the preoperative data and the intraoperative data, transmit the operating information to the augmented reality system, and compensate in real-time for the deformation of the anatomical structure according to a deformation engine.

In one example, the deformation engine automatically compensates for the deformation of the anatomical structure by aligning the preoperative data with the intraoperative data through artificial intelligence and machine learning before the computer system transmits the plurality of operating information to the augmented reality system. In another example, the deformation engine manually compensates for the deformation of the anatomical structure by allowing the user to manually align the preoperative data with the intraoperative data. In other various examples, the computer system includes a graphics and physics engine configured to set upper boundary conditions and lower boundary conditions on the preoperative data based on characteristics of the anatomical structure. The computer system can generate the fused data by super-imposing the intraoperative data over the preoperative data or super-imposing the preoperative data over the intraoperative data.

In another embodiment, a method for holographic augmented reality visualization and guidance in performing a medical procedure on a patient by a user includes providing a system having an augmented reality system configured to display a plurality of operating information of the patient in an augmented reality environment, a first holographic image acquisition system, a second holographic image acquisition system, and a computer system having a deformation engine. Preoperative data from the patient can be acquired by the first holographic image acquisition system. Intraoperative data from the patient can be acquired by the second holographic image acquisition system. The preoperative data to the plurality of operating information can be selectively registered. The intraoperative data to the plurality of operating information can be selectively registered. Fused data can be selectively generated by the computer system. The preoperative data can be selectively adjusted according to the deformation engine, where the preoperative data does not align with the intraoperative data. The plurality of operating information can be transmitted to the augmented reality system by the computer system. The intraoperative data can be selectively displayed by the augmented reality system, where the intraoperative data permits the user to navigate a body of a patient. The preoperative data can be selectively displayed by the augmented reality system, where the intraoperative data does not substantially permit the user to navigate the body of the patient. The fused data can be selectively displayed by the augmented reality system, where both the preoperative data and the intraoperative data permit the user to navigate the body of the patient. The plurality of operating information can be selectively adjusted by the user in real-time.

Systems and methods provided herein can include various aspects. In certain embodiments, the first holographic image acquisition system can be selected from a group consisting of a computerized tomography (CT) apparatus, cone beam computed tomography (CBCT) apparatus, a magnetic resonance imaging (MM) apparatus, a protectional radiography apparatus, a positron emission tomography (PET) apparatus, a volumetric ultrasound and fluoroscopy system, and combinations thereof. In certain embodiments, the second holographic image acquisition system can be selected from a group consisting of a general ultrasound, a transesophageal ultrasound, an endoscopic ultrasound, a point of care ultrasound, an ultrasound echocardiogram (ECG) imaging apparatus, a fluoroscopy apparatus, a transthoracic echocardiogram (TTE), a transesophageal echocardiogram (TEE), an intracardiac echocardiogram (ICE), and combinations thereof. In certain embodiments, the computer system can include a graphics and physics engine configured to set upper boundary conditions and lower boundary conditions on the preoperative data based on characteristics of the preoperative data.

In another embodiment, a method for holographic augmented reality visualization and guidance in performing a medical procedure on a patient by a user includes providing a computer system, capturing preoperative data of an anatomical structure of the patient, and capturing intraoperative data of the anatomical structure of the patient with a probe during the medical procedure. The preoperative data and the intraoperative data can be cross-referenced. Next, the preoperative data is segmented in real time during the medical procedure and then the segmented preoperative data and the intraoperative data are registered, by the computer system, in real time during the medical procedure. Next, the segmented preoperative data and the intraoperative data are transmitted, by the computer system, to an augmented reality system, in real time. The preoperative data and the intraoperative data are displayed by the augmented reality system, in real time during the medical procedure.

Systems and methods provided herein can include various aspects. In certain embodiments, the method can include identifying, by the computer system, deformations of a profile of the anatomical structure in the preoperative data. In certain embodiments, the computer system can include a deformation engine configured to automatically compensate for the identified deformation of the anatomical structure by aligning the preoperative data with the intraoperative data through artificial intelligence and machine learning. Alternatively, the deformation engine is configured to allow the user to manually align the preoperative data with the intraoperative data. In certain embodiments, the computer system includes a graphics and physics engine configured to set upper boundary conditions and lower boundary conditions on the preoperative data based on characteristics of the anatomical structure. In certain embodiments, the computer system includes a deformation engine configured to adjust the identified deformation of the anatomical structure by allowing the user to manually align the preoperative data with the intraoperative data within the upper boundary conditions and lower boundary conditions. In certain embodiments, capturing the preoperative data can include capturing computed tomography image data, and/or capturing the intraoperative data can include capturing ultrasound imaging. The method can include super-imposing the intraoperative data over the preoperative data to identify changes that can occur between the preoperative data and the intraoperative data and/or super-imposing the preoperative data over the intraoperative data to identify changes that can occur between the preoperative data and the intraoperative data.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figures 4A, 4B, 4C:
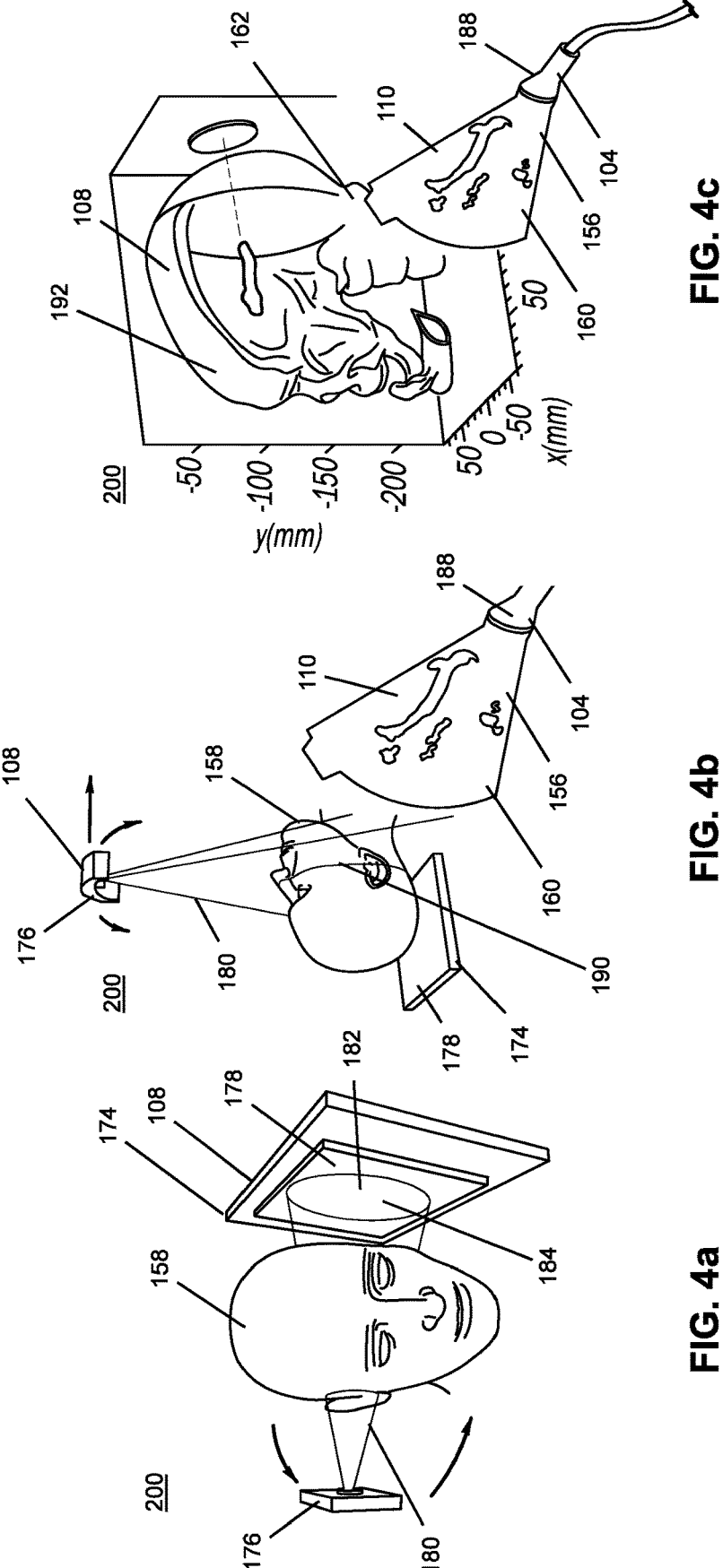
Figure 5:
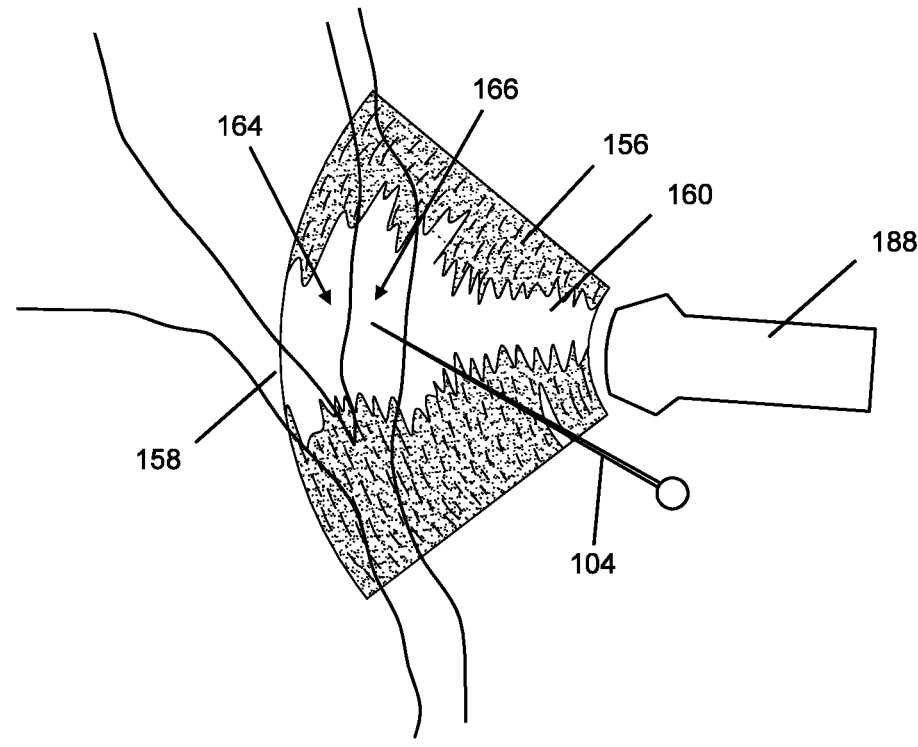
Figure 6:
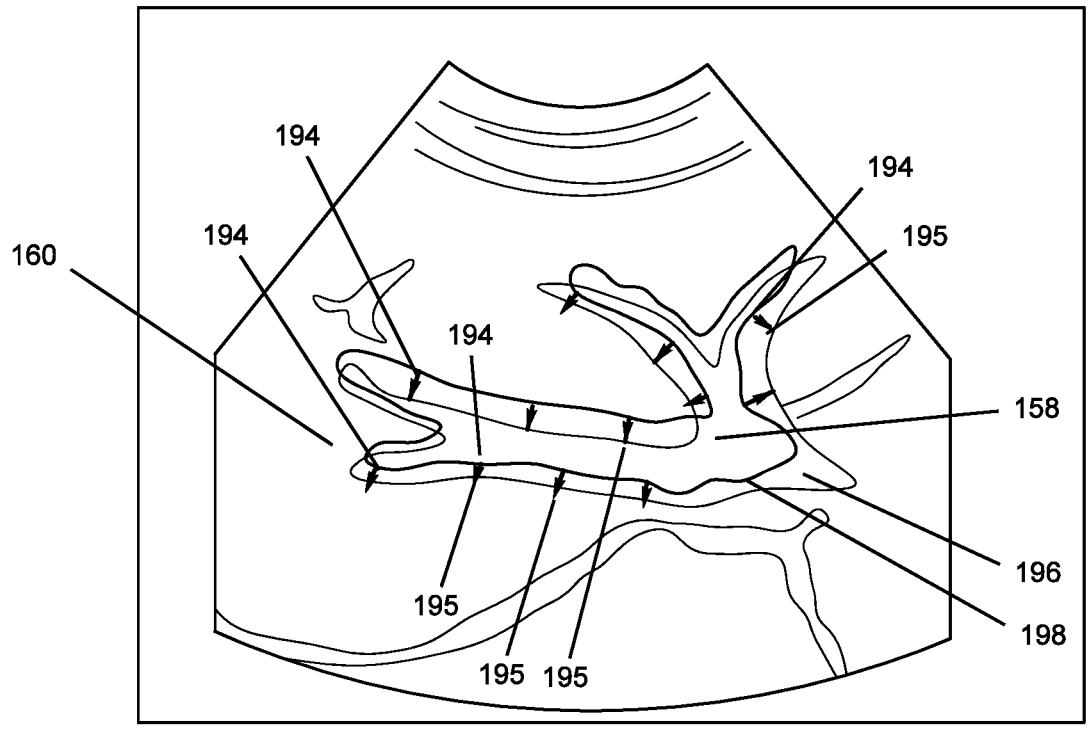
Figure 7:
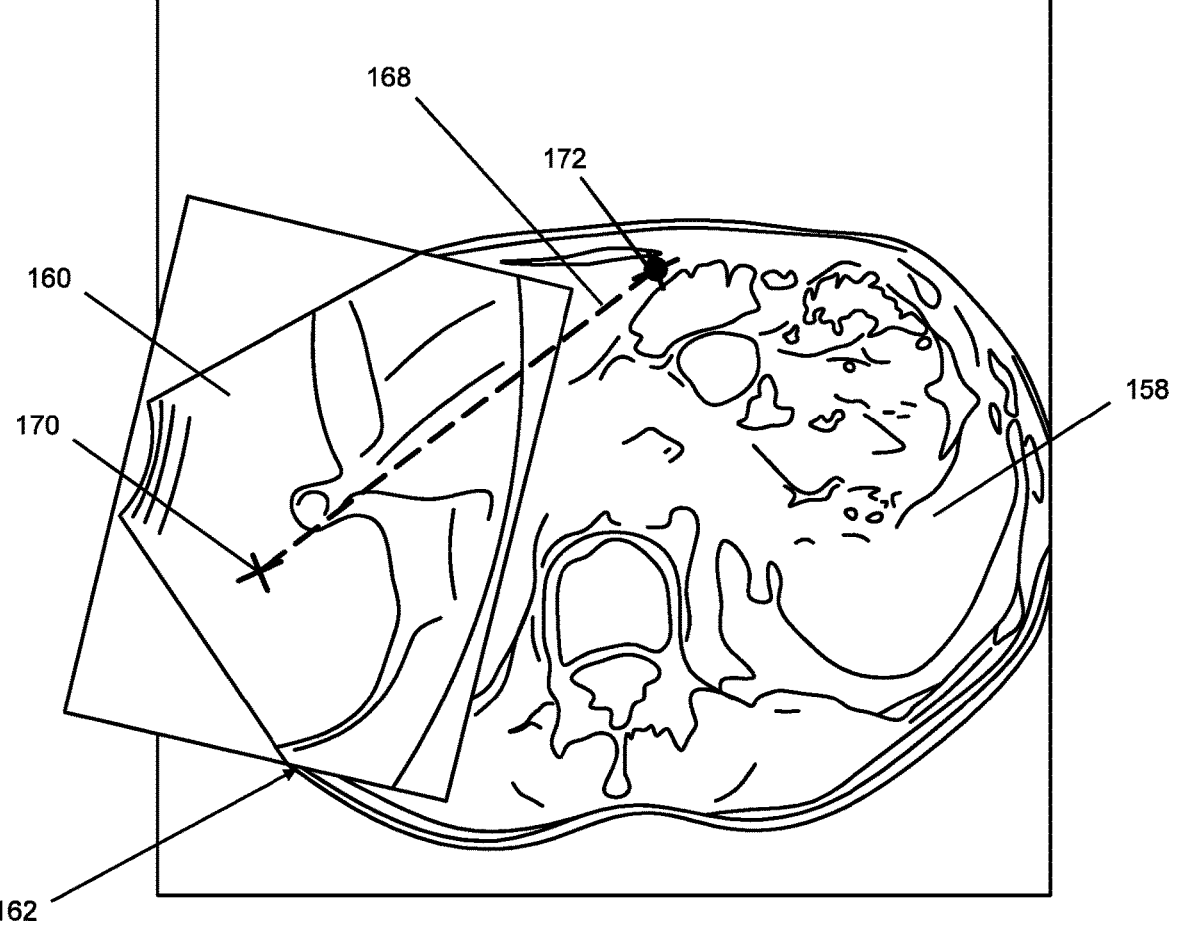
Figure 8:
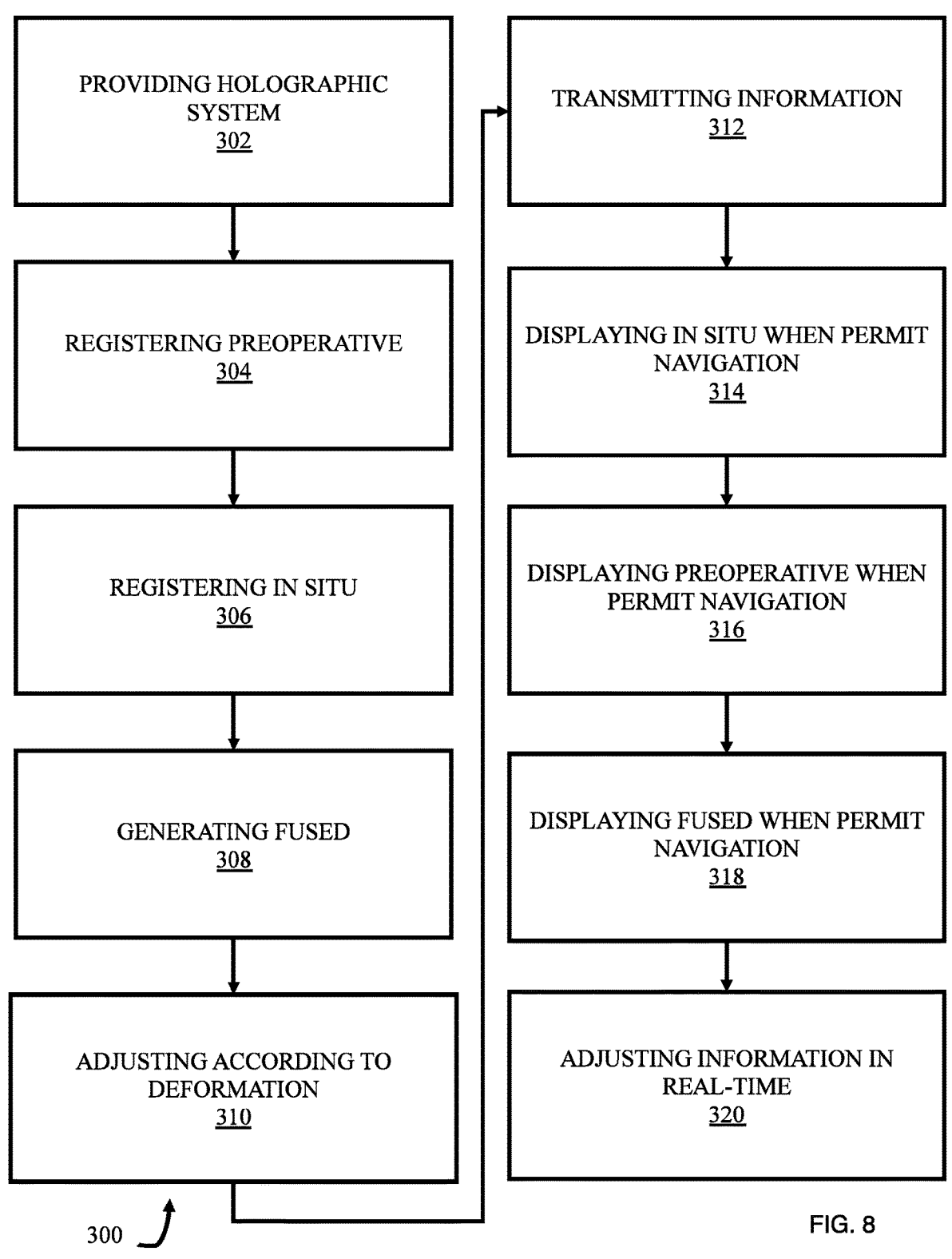

FIGS. 4a-4c schematically depicts an automatic segmentation and registration process according to the present disclosure;

FIG. 5 schematically depicts preoperative data superimposed over intraoperative data according to the present disclosure;

FIG. 6 schematically depicts the system in operation, according to certain embodiments, showing a fused data displayed in an augmented reality environment;

FIG. 7 schematically depicts intraoperative data superimposed over preoperative data according to the present disclosure; and FIG. 8 is a flowchart illustrating a method for using the system for automatic segmentation and registration.

DETAILED DESCRIPTION

The following description of technology is merely exemplary in nature of the subject matter, manufacture, and use of one or more inventions, and is not intended to limit the scope, application, or uses of any specific invention claimed in this application or in such other applications as can be filed claiming priority to this application, or patents issuing therefrom. Regarding methods disclosed, the order of the steps presented is exemplary in nature, and thus, the order of the steps can be different in various embodiments, including where certain steps can be simultaneously performed.

The terms "a" and "an" as used herein indicate "at least one" of the item is present; a plurality of such items can be present, when possible. Except where otherwise expressly indicated, all numerical quantities in this description are to be understood as modified by the word "about" and all geometric and spatial descriptors are to be understood as modified by the word "substantially" in describing the broadest scope of the technology. The term "about" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that can arise from ordinary methods of measuring or using such parameters.

Although the open-ended term "comprising," as a synonym of non-restrictive terms such as including, containing, or having, is used herein to describe and claim embodiments of the present technology, embodiments can alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application.

Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter can define endpoints for a range of values that can be claimed for the parameter. For example, if Parameter X is exemplified herein to have value A and also exemplified to have value Z, it is envisioned that Parameter X can have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X can have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it can be directly on, engaged, connected, or coupled to the other element or layer, or intervening elements or layers can be present. In contrast, when an element is referred to as being "directly on," "directly engaged to," "directly connected to" or "directly coupled to" another element or layer, there can be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, layers and/or sections, these elements, components, regions, layers and/or sections should not be limited by these terms. These terms can be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, can be used herein for ease of description to describe one element or feature's relationship to another element(s) or feature(s) as illustrated in the figures. Spatially relative terms can be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

All documents, including patents, patent applications, and scientific literature cited in this detailed description are incorporated herein by reference, unless otherwise expressly indicated. Where any conflict or ambiguity can exist between a document incorporated by reference and this detailed description, the present detailed description controls.

As used herein, the term "anatomical structures" can include nerves, blood vessels, tumors, connective tissues, and cancerous tumors. It should be appreciated that anatomical structures can also include other structures within a body of a patient, within the scope of this disclosure.

As used herein, the term "percutaneous" refers to something that is made, done, or effected through the skin.

As used herein, the term "percutaneous medical procedure" refers to accessing the internal organs or tissues via needle-puncture of the skin, rather than by using an open approach where the internal organs or tissues are exposed (typically with a scalpel).

As used herein, the term "non-vascular" when used with "percutaneous medical procedure" refers to a medical procedure performed on any portion of the subject's body distinct from the vasculature that is accessed percutaneously. Examples of percutaneous medical procedures can include a biopsy, a tissue ablation, a cryotherapy procedure, a brachytherapy procedure, an endovascular procedure, a drainage procedure an orthopedic procedure, a pain management procedure, a vertebroplasty procedure, a pedicle/screw placement procedure, a guidewire-placement procedure, a SI-Joint fixation procedure, a training procedure, or the like.

As used herein, the term "endovascular" when used with "percutaneous medical procedure" refers to a medical procedure performed on a blood vessel (or the lymphatic system) accessed percutaneously. Examples of endovascular percutaneous medical procedures can include an aneurism repair, a stent grafting/placement, a placement of an endovascular prosthesis, a placement of a wire, a catheterization, a filter placement, an angioplasty, or the like.

As used herein, the terms "interventional device" or "tracked instrument" refers to a medical instrument used during the non-vascular percutaneous medical procedure.

As used herein, the term "tracking system" refers to something used to observe one or more objects undergoing motion and supply a timely ordered sequence of tracking data (e.g., location data, orientation data, or the like) in a tracking coordinate system for further processing. As an example, the tracking system can be an electromagnetic tracking system that can observe an interventional device equipped with a sensor-coil as the interventional device moves through a patient's body.

As used herein, the term "tracking data" refers to information recorded by the tracking system related to an observation of one or more objects undergoing motion.

As used herein, the term "tracking coordinate system" refers to a 3D Cartesian coordinate system that uses one or more numbers to determine the position of points or other geometric elements unique to the particular tracking system. For example, the tracking coordinate system can be rotated, scaled, or the like, from a standard 3D Cartesian coordinate system.

As used herein, the term "head-mounted device" or "headset" or "HMD" refers to a display device, configured to be worn on the head, that has one or more display optics (including lenses) in front of one or more eyes. These terms may be referred to even more generally by the term "augmented reality system," although it should be appreciated that the term "augmented reality system" is not limited to display devices configured to be worn on the head. In some instances, the head-mounted device can also include a non-transitory memory and a processing unit. An example of a suitable head-mounted device is a Microsoft HoloLens®.

As used herein, the terms "imaging system," "image acquisition apparatus," "image acquisition system" or the like refer to technology that creates a visual representation of the interior of a patient's body. For example, the imaging system can be a computed tomography (CT) system, a fluoroscopy system, a magnetic resonance imaging (MRI) system, an ultrasound (US) system, or the like.

As used herein, the terms "coordinate system" or "augmented realty system coordinate system" refer to a 3D Cartesian coordinate system that uses one or more numbers to determine the position of points or other geometric elements unique to the particular augmented reality system or image acquisition system to which it pertains. For example, the headset coordinate system can be rotated, scaled, or the like, from a standard 3D Cartesian coordinate system.

As used herein, the terms "image data" or "image dataset" or "imaging data" refers to information recorded in 3D by the imaging system related to an observation of the interior of the patient's body. For example, the "image data" or "image dataset" can include processed two-dimensional or three-dimensional images or models such as tomographic images, e.g., represented by data formatted according to the Digital Imaging and Communications in Medicine (DICOM) standard or other relevant imaging standards.

As used herein, the terms "imaging coordinate system" or "image acquisition system coordinate system" refers to a 3D Cartesian coordinate system that uses one or more numbers to determine the position of points or other geometric elements unique to the particular imaging system. For example, the imaging coordinate system can be rotated, scaled, or the like, from a standard 3D Cartesian coordinate system.

As used herein, the terms "hologram", "holographic," "holographic projection", or "holographic representation" refer to a computer-generated image projected to a lens of a headset. Generally, a hologram can be generated synthetically (in an augmented reality (AR)) and is not related to physical reality.

As used herein, the term "physical" refers to something real. Something that is physical is not holographic (or not computer-generated).

As used herein, the term "two-dimensional" or "2D" refers to something represented in two physical dimensions.

As used herein, the term "three-dimensional" or "3D" refers to something represented in three physical dimensions. An element that is "4D" (e.g., 3D plus a time and/or motion dimension) would be encompassed by the definition of three-dimensional or 3D.

As used herein, the term "integrated" can refer to two things being linked or coordinated. For example, a coil-sensor can be integrated with an interventional device.

As used herein, the term "degrees-of-freedom" or "DOF" refers to a number of independently variable factors. For example, a tracking system can have six degrees-of-freedom (6DOF), a 3D point and 3 dimensions of rotation.

As used herein, the term "real-time" refers to the actual time during which a process or event occurs. In other words, a real-time event is done live (within milliseconds so that results are available immediately as feedback). For example, a real-time event can be represented within 100 milliseconds of the event occurring.

As used herein, the terms "subject" and "patient" can be used interchangeably and refer to any vertebrate organism.

As used herein, the term "registration" refers to steps of transforming tracking data and body image data to a common coordinate system and creating a holographic display of images and information relative to a body of a physical patient during a procedure, for example, as further described in U.S. Patent Application Publication No. 2018/0303563 to West et al., and also applicant's co-owned U.S. patent application Ser. No. 17/110,991 to Black et al. and U.S. patent application Ser. No. 17/117,841 to Martin III et al., the entire disclosures of which are incorporated herein by reference.

Figure 1:
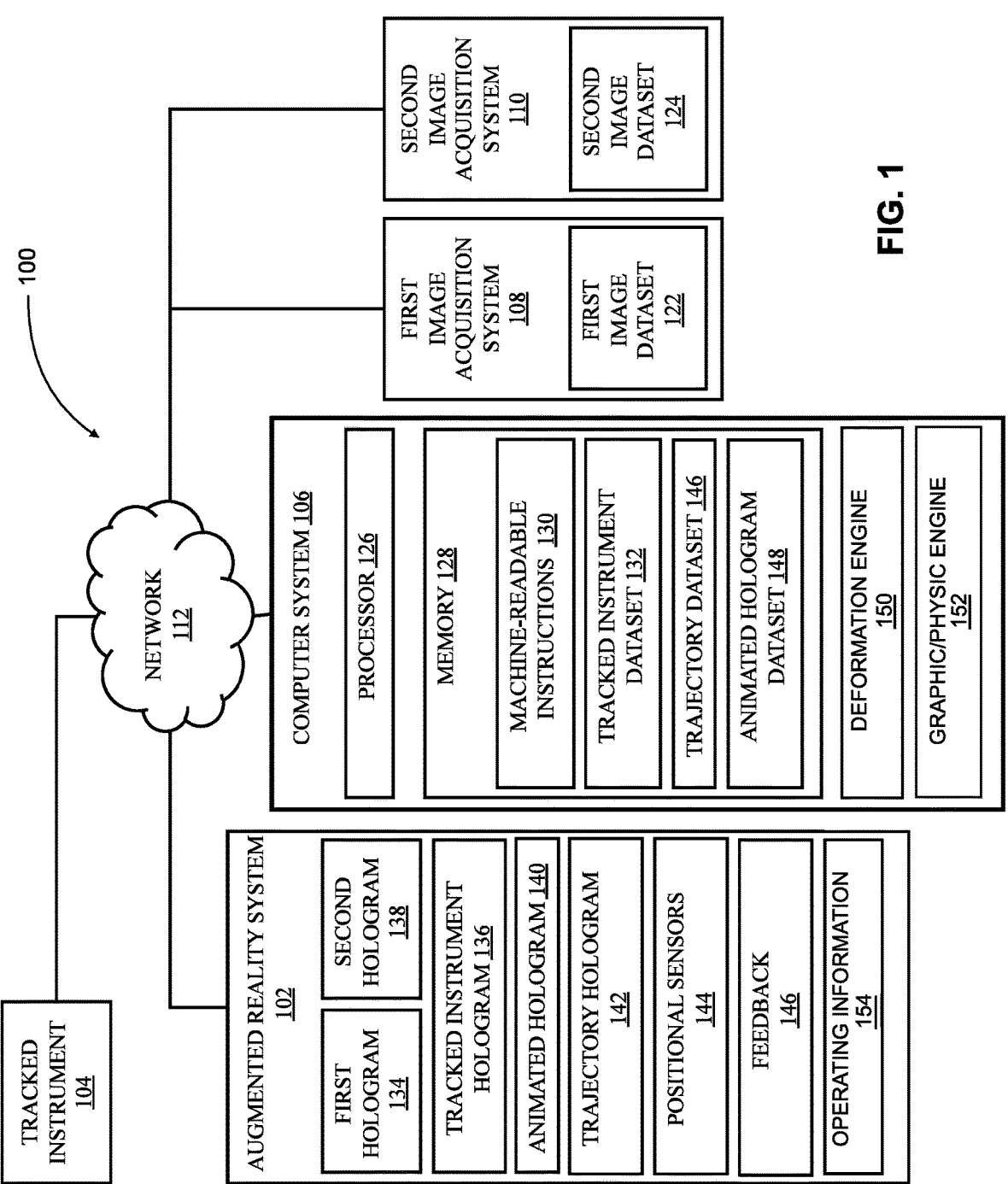
FIG. 1 is a schematic view of a system, according to certain embodiments of the present disclosure, showing an augmented reality system, an imaging system, a measuring system, and a computer system.

Referring to FIG. 1, a system 100 for holographic augmented reality visualization and guidance in performing a medical procedure on an anatomical site of a patient by a user includes an augmented reality system 102, a tracked instrument 104, a computer system 106, and a first image acquisition system 108. In certain embodiments, the system 100 can further include a second image acquisition system 110, a deformation engine 150, a graphic and physic engine

152, and/or a plurality of operating information 154. Each one of the augmented reality system 102, the tracked instrument 104, the first image acquisition system 108, the second image acquisition system 110 can be selectively or permanently in communication with the computer system 106, for example, via a computer network 112. Other suitable instruments, tools, equipment, sub-systems, and the like for use with the system 100, as well as other network means including wired and wireless means of communication between the components of the system 100, can also be employed by the skilled artisan, as desired.

Figure 2:
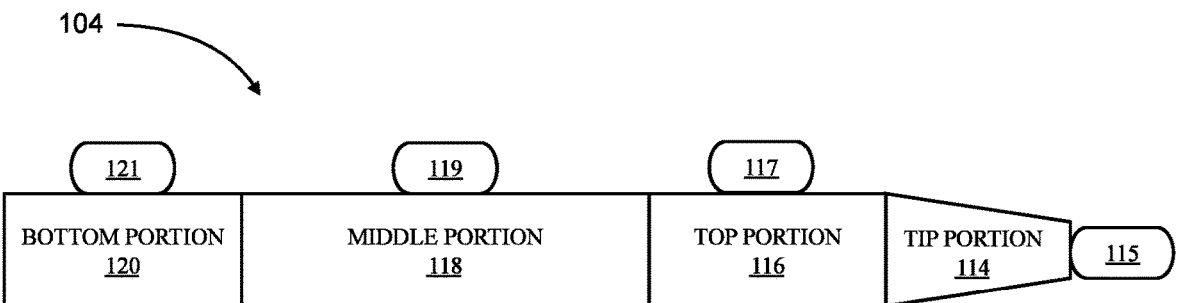
FIG. 2 is a schematic depiction of a tracked instrument according to the present disclosure.

Referring to FIG. 2, the tracked instrument 104 can be an interventional device that is sensorized so that both a location and an orientation of the tracked instrument 104 can be determined by the computer system 106. In particular, the tracked instrument 104 can have an elongated body, such as long flexible tube, with a plurality of portions 114, 116, 118, 120 disposed along a length of the elongated body, which in turn can each have one of a plurality of sensors 115, 117, 119, 121. For example, the tracked instrument 104 can have a tip portion 114, a top portion 116, a middle portion 118, and a bottom portion 120. A tip sensor 115 can be disposed at the tip portion 114 of the tracked instrument 104. A top portion sensor 117 can be disposed at the top portion 116 of the tracked instrument 104. A middle portion sensor 119 can be disposed at the middle portion 118 of the tracked instrument 104. A bottom portion sensor 121 can be disposed at the bottom portion 120 of the tracked instrument 104. Each of the sensors 115, 117, 119, 121 can be in communication with or otherwise detectable by the computer system 106.

It should be appreciated that the tracking provided by the tip sensor 115 is especially advantageous as this can be used by the user as a preselected reference point for the tracked instrument 104. The preselected reference point can be configured to be an anchoring point for a trajectory hologram (shown in FIG. 1 and described herein as "142") such as a holographic light ray that can be generated by the augmented reality system 102. The holographic light ray can assist the user with the alignment and movement of the tracked instrument 104 along a preferred pathway or trajectory, as described further herein. It should be appreciated that one skilled in the art can also select any number of preselected reference points, within the scope of this disclosure. In certain embodiments, the preselected reference point can be adjusted in real-time by the user during the medical procedure and can alternatively be based on one or more of the other sensors 115, 117, 119, 121, as desired.

In certain examples, the sensors 115, 117, 119, 121 can be part of an electromagnetic (EM) tracking system that can be part of and/or used by the computer system 106 to detect the location and the orientation of a physical tracked instrument 104. For example, the sensors 115, 117, 119, 121 can include one or more sensor-coils. The computer system 106 can detect the one or more sensor-coils and provide tracking data (e.g., with six degrees of freedom) in response to the detection. For example, the tracking data can include real-time 3D position data and real-time 3D orientation data. The tracking system of the computer system 106 can also detect coil-sensors that are not located on the physical tracked instrument 104 or physical interventional device, such as one or more sensors located on fiducial markers or other imaging targets.

Further, the sensors 115, 117, 119, 121 can be configured to assess various additional information of the tracked instrument 104, such as angular velocity and acceleration of the tracked instrument 104. Nonlimiting examples of sensors 115, 117, 119, 121 suitable for determining angular velocity and acceleration include accelerometers, gyroscopes, electromagnetic sensors, and optical tracking sensors. Notably, use of electromagnetic sensors can enable more precise real-time object tracking of small objects without line-of-sight restrictions.

Other suitable tracking systems, such as optical tracking systems, can be used in conjunction with the augmented reality system 102 and the computer system 106. Embodiments where the tracked instrument 104 can communicate by transmission wirelessly or through a wired connection with the augmented reality system 102 and the computer system 106 are contemplated. It should also be appreciated that a skilled artisan can employ mixed types of sensors 115, 117, 119, 121, as desired.

The tracked instrument 104 can include the following aspects, which can depend on the type of medical procedure being performed, the anatomical site of the patient, and/or a particular step of the medical procedure being performed. Non-limiting examples of the tracked instrument 104 includes a catheter, an orthopedic tool, a tool used to install, adjust, or remove an implant, an ablation probe, a laparoscopic instrument, and/or intervention tools. One of ordinary skill in the art can employ other suitable interventional devices for the tracked instrument 104, depending on the desired procedure or a particular step of the desired procedure, within the scope of the present disclosure.

With renewed reference to FIG. 1, the first image acquisition system 108 can be configured to acquire a first holographic image dataset 122 from the patient. In particular, the first image acquisition system 108 can be configured to acquire the first holographic image dataset 122 from the patient in a preoperative manner. In certain embodiments, the first image acquisition system 108 can include one or more of a computerized tomography (CT) apparatus, cone beam computed tomography (CBCT) apparatus, a magnetic resonance imaging (Mill) apparatus, a projectional radiography apparatus, a positron emission tomography (PET) apparatus, and a volumetric ultrasound and fluoroscopy system. Other suitable types of instrumentation for the first image acquisition system 108 can also be employed, as desired. It is further possible to have the first image acquisition system 108 include multiple image acquisitions, including fused images, by the same or different imaging means, where the first image dataset 122 can therefore include multiple and/or fused images from the same or different imaging means.

Likewise, the second image acquisition system 110 can be configured to acquire a second holographic image dataset 124 from the patient. In particular, the second image acquisition system 110 can be configured to acquire the second holographic image dataset 124 from the patient in an intraoperative manner, and most particularly in real-time as the procedure is being undertaken. In certain embodiments, the second image acquisition system 110 can include one or more ultrasound systems, including a general ultrasound, a transesophageal ultrasound, an endoscopic ultrasound, a point of care ultrasound, an ultrasound echocardiogram (ECG) imaging apparatus, a fluoroscopy apparatus, as well as other active or real-time imaging systems. Further embodiments include where the second holographic image dataset 124 can be acquired by a predetermined modality including one of a transthoracic echocardiogram (TTE), a transesophageal echocardiogram (TEE), and an intracardiac echocardiogram (ICE). Other suitable types of instrumentation and modalities for the second image acquisition system 110 can also be employed, as desired. It is further possible to have the second image acquisition system 110 include multiple image acquisitions, including fused images, by the same or different imaging means, where the second image dataset 124 can therefore include multiple and/or fused images from the same or different imaging means.

Although use of both the first image acquisition system 108 and the second image acquisition system 110 is shown and described herein, embodiments in which only one or the other of the first image acquisition system 108 and the second image acquisition system 110 is employed, are considered to be within the scope of the present disclosure.

With continued reference to FIG. 1, the computer system 106 can include a processor 126 configured to perform functions associated with the operation of the system 100 for holographic augmented reality visualization and guidance. The processor 126 can include one or more types of general or specific purpose processors. In certain embodiments, multiple processors 126 can be utilized. The processor 126 can include one or more of general-purpose computers, special purpose computers, microprocessors, digital signal processors (DSPs), field-programmable gate arrays (FP-GAs), application-specific integrated circuits (ASICs), and processors based on a multi-core processor architecture, as non-limiting examples.

The computer system 106 can include a memory 128 on which tangible, non-transitory, machine-readable instructions 130 can be stored. The memory 128 can include one or more types of memory and can include any type suitable to the local application environment. Examples include where the memory 128 can include various implementations of volatile and/or nonvolatile data storage technology, such as a semiconductor-based memory device, a magnetic memory device and system, an optical memory device and system, fixed memory, and removable memory. For example, the memory 128 can include one or more of random-access memory (RAM), read only memory (ROM), static storage such as a magnetic or optical disk, hard disk drive (HDD), or any other type of non-transitory machine or computer readable media, as well as combinations of the aforementioned types of memory. Instructions stored in the memory 128 can include program instructions or computer program code that, when executed by the processor 126, enables the system 100 to perform tasks as described herein.

The machine-readable instructions 130 can include one or more various modules. Such modules can be implemented as one or more of functional logic, hardware logic, electronic circuitry, software modules, and the like. The modules can include one or more of an augmented reality system module, an image acquiring module, an instrument tracking module, an image dataset registering module, a hologram rendering module, an image registering module, a trajectory hologram rendering module, and/or other suitable modules, as desired.

The computer system 106 can be in communication with the augmented reality system 102, the tracked instrument 104, the first image acquisition system 108, and the second image acquisition system 110, for example, via the network 112, and can be configured by the machine-readable instructions 130 to operate in accordance with various methods for holographic augmented reality visualization and guidance in performing a medical procedure on an anatomical site of a patient by a user as described further herein. The computer system 106 can be separately provided and spaced apart from the augmented reality system 102, or the computer system 106 can be provided together with the augmented reality system 102 as a singular one-piece unit or integrated with other systems, as desired.

It should be appreciated that the network 112 of the system 100 can include various wireless and wired communication networks, including a radio access network, such as LTE or 5G, a local area network (LAN), a wide area network (WAN) such as the Internet, or wireless LAN (WLAN), as non-limiting examples. It will be appreciated that such network examples are not intended to be limiting, and that the scope of this disclosure includes implementations in which one or more computing platforms of the system 100 can be operatively linked via some other communication coupling, including combinations of wireless and wired communication networks. One or more components and subcomponents of the system 100 can be configured to communicate with the networked environment via wireless or wired connections. In certain embodiments, one or more computing platforms can be configured to communicate directly with each other via wireless or wired connections. Examples of various computing platforms and networked devices include, but are not limited to, smartphones, wearable devices, tablets, laptop computers, desktop computers, Internet of Things (IoT) devices, or other mobile or stationary devices such as standalone servers, networked servers, or an array of servers.

In certain embodiments, the computer system 106 can be configured to track the tracked instrument 104 using the plurality of sensors 115, 117, 119, 121 to provide a tracked instrument dataset 132. The tracked instrument dataset 132 can be stored using the memory 128. In particular, the tracked instrument dataset 132 can include the location and the orientation of the tracked instrument 104 in physical space, for example.

The computer system 106 can also be configured to register the first holographic image dataset 122 from the first image acquisition system 108 and the tracked instrument dataset 132 obtained by the computer system 106 with the patient, as also described herein.

Figure 3:
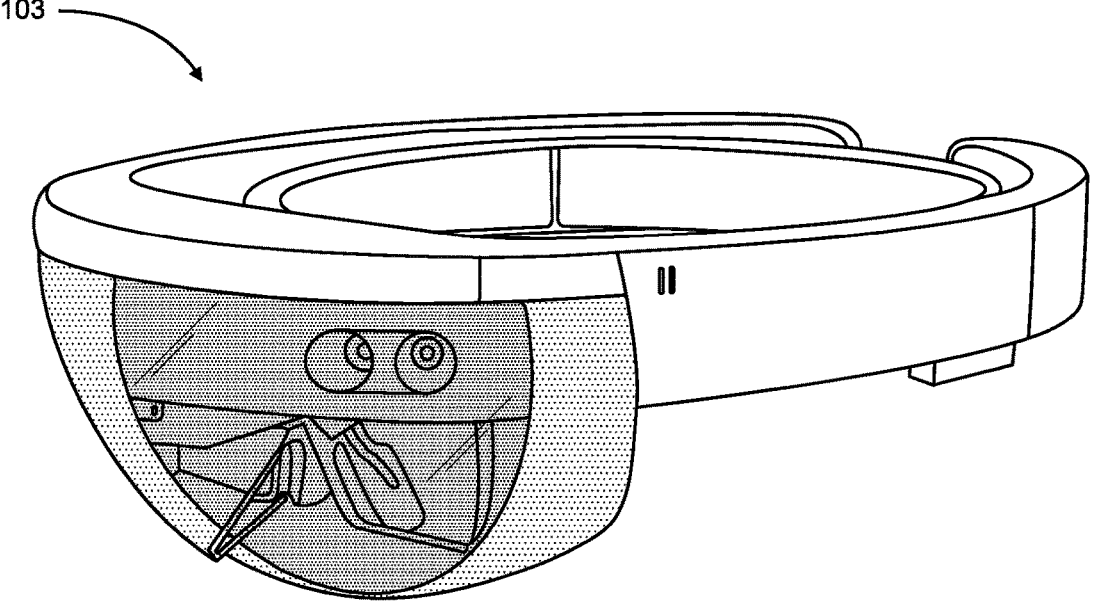
FIG. 3 is a side view of a head mounted device according to the present disclosure.

With reference to FIG. 3, and continued reference to FIG. 1, the augmented reality system 102 can be configured to render a plurality of holograms 134, 136, 138, 140, 142 in operation of the system 100 in accordance with the present disclosure. In particular, the augmented reality system 102 can include a mixed reality (MR) display. For example, the MR display can include MR smart glasses or MR head-mounted displays 103, as illustrated in FIG. 3. Nonlimiting examples of the augmented reality system 102 can include the Magic Leap One® or versions of the Microsoft Holo-Lens®. It should be appreciated that other types of MR displays can be used for the augmented reality system 102, as long as they are capable of superimposing computer-generated imagery, including holograms, over real-world objects. Non-limiting examples of real-world objects include a body of the patient, the operating table, or empty space. Additionally, although the augmented reality system 102 can be described primarily as including a head-mounted display 103, it should be understood that other types of displays that are not head-mounted, but which are capable of generating and superimposing holograms 134, 136, 138, 140 over real-world views, can also be employed, as desired.

The augmented reality system 102 and the computer system 106 can be integrated into either a single component or can be separate components that communicate through a local network 112. It should be appreciated that in instances where the augmented reality system 102 is not integrated with or does not contain the computer system 106, the augmented reality system 102 can further include an additional non-transitory memory and a processing unit (that can include one or more hardware processors) that can aid in the rendering or generation of holograms 134, 136, 138, 140, 142. The augmented reality system 102 can also include a recording means or camera to record one or more images, one or more image-generation components to generate/display a visualization of the holograms 134, 136, 138, 140, 142, and/or other visualization and/or recording elements. Likewise, the augmented reality system 102 can transmit images, recordings, and/or videos of one or more nonaugmented views, holograms 134, 136, 138, 140, 142, and/or mixed reality views to the computer system 106 for storage or recording, whether the computer system 106 is local or remote from the augmented reality system 102.

It should be appreciated that in certain embodiments the augmented reality system 102 can also include one or more positional sensors 144. One or more positional sensors 144 of the augmented reality system 102 can be configured to determine various positional information for the augmented reality system 102, such as the approximated position in three-dimensional (3D) space, the orientation, angular velocity, and acceleration of the augmented reality system 102. For example, it should be understood that this can allow the holographic imagery to be accurately displayed within the field of view of the user, in operation. Nonlimiting examples of the positional sensors 144 include accelerometers, gyroscopes, electromagnetic sensors, and/or optical tracking sensors. It should further be appreciated that a skilled artisan can employ different types and numbers of positional sensors 144 of the augmented reality system 102, for example, as required by the procedure or situation within which the augmented reality system 102 is being used.

As shown in FIG. 1, for example, the holograms 134, 136, 138, 140, 142 generated by the augmented reality system 102 can include one or more of a first hologram 134, a tracked instrument hologram 136, a second hologram 138, an animated hologram 140, and a trajectory hologram 142. The first hologram 134 generated by the augmented reality system 102 can be based on the first holographic image dataset 122 from the patient. The tracked instrument hologram 136 generated by the augmented reality system 102 can be based on the tracked instrument dataset 132. The second hologram 138 generated by the augmented reality system 102 can be based on the second holographic image dataset 124. The animated hologram 140 can be based on a processing by the computer system 106 of the second holographic image dataset 124 to provide an animated hologram dataset 148, as described herein. The trajectory hologram 142 can be based on a trajectory dataset 146, which can be either manually or automatically selected and stored in the memory 128 of the computer system 106, as described herein.

Referring to FIGS. 4a-7 the augmented reality system 102 can also be configured to display a plurality of operating information 154 to the user. The computer system 106 can be in communication with the augmented reality system 102. The computer system 106 can be configured to store and generate the operating information 154, either through manual intervention by the user and/or other medical professionals or automatically based on machine-readable instructions 130 encoded within the memory 128. For example, the operating information 154 can be generated in the augmented reality system 102 depending on a sensor-determined position and/or orientation of the tracked instrument 104, such as by using algorithms, artificial intelligence (AI) protocols, or other user-inputted data or thresholds. In addition, the computer system 106 can be further configured to permit the user to selectively adjust the plurality of operating information 154 in real-time. Desirably, this can permit the user the freedom to select which information will be displayed. For example, the user can adjust the position or orientation of the trajectory hologram 142. In addition, the user can decide which of the operating information 154 or data is actively being shown. It should be appreciated that other settings and attributes of the operating information 154 can be adjusted by the user in real-time, within the scope of this disclosure. In addition, it should be appreciated that a person skilled in the art can employ other features within the computer system 106, within the scope of this disclosure.

The augmented reality system 102 can be configured to capture a real-world view of the environment around the augmented reality system 102. The augmented reality system 102 intercepts the real-world view and re-displays the real-world view to the user with the plurality of operating information. The plurality of operating information 154 can be holographic projections that are super-imposed on real-world objects. Non-limiting examples of real-world objects include a body of the patient, an operating table, or empty space. It should be appreciated that the plurality of operating information 154 can be super-imposed on other real-world objects, within the scope of this disclosure. The augmented reality system 102 can project the operating information 154 within a field of view of the user, adjacent to various real-world objects, as well as overlaid upon or highlighting real-world objects, such as one or more portions of the anatomical site of the patient, the tracked instrument 104, or the various holograms 134, 136, 138, 140, 142. The operating information 154 can include real-time navigation instructions or guidance for the trajectory to be employed, for example. It should be appreciated that the augmented reality system 102 can super-impose the operating information 154 over various real-world objects such as the tracked instrument 104 or in an area adjacent to the tracked instrument 104, as well as over the various holograms 134, 136, 138, 140, 142 rendered, as desired. Advantageously, generation of such operating information 154 or details allows the user to simultaneously view the patient and the plurality of operating information 154 in the same field of view. Also, generation of the operating information 154 or details together with the various holograms 134, 136, 138, 140, 142 permits the user to plan, size, or pre-orient the tracked instrument 104, in operation.

As shown in FIGS. 4a-4c, in one specific example, ultrasound imaging 156 from an ultrasound procedure can be directly super-imposed as a cone emitting from an instrument 104, namely, an ultrasound probe. Advantageously, this can permit the user to view the ultrasound imaging 156 within the same field of view as the instrument 104, instead of having to glance at a monitor outside of the field of view of the user. Non-limiting examples of the instrument 104 include implants, needles, ultrasound probes, catheters, stents, mechanical heart values, and biological heart valves. It should be appreciated that a skilled artisan can employ different types of instruments within the scope of this disclosure.

With continued reference to FIGS. 4a-c, the plurality of operating information 154 can have at least one of preoperative data 158, intraoperative data 160, and fused data 162. Preoperative data 158 can include information related to the patient obtained prior to the medical procedure, for example, using the first holographic image acquisition system 108 as well as data obtained, processed, and/or annotated from a variety of sources. Embodiments of preoperative data 158 include various images, fused images, annotated images, as well as one or more markers or flagged points or portions of the anatomical site of the patient. Nonlimiting examples of preoperative data 158 include static images or recordings relating to computed tomography (CT) imaging, cone beam computed tomography (CBCT) imagining, magnetic resonance imaging (MRI), positron emission tomography (PET) imagining, and/or volumetric ultrasound and fluoroscopy imaging. It should be appreciated that the preoperative data 158 can include information from other diagnostic medical procedures, imaging modalities, and modeling systems, as desired.

The preoperative data 158 can be configured to provide the user with references and guides during a medical procedure based on the preoperative data 158 obtained in previous medical procedures and/or imagining. The augmented reality system 102 can display the preoperative data 158 over the body of the patient and align the projected preoperative data 158, so it correlates and corresponds with the correct anatomical structure of the patient. Desirably, this can permit the user to use the preoperative data 158 as a reference to navigate the body of the patient.

Referring to FIG. 5, preoperative data 158 can be displayed when the preoperative data 158 is better suited to be the navigational guide, due to defects in the intraoperative data 160. For example, if the ultrasound imaging 156 is unable to detect a particular anatomical structure in the body, the preoperative data 158 can be instead displayed to show the particular anatomical structure using imaging from the preoperative data 158. As shown in FIG. 5, an anatomical structure is creating an obstructed area 164 in the ultrasound imaging 156 thereby rendering the target anatomical structure 166 (e.g., a hepatic vein of a liver) undetectable. The augmented reality system 102 can retrieve a preoperative CT image (preoperative data 158) of the hepatic vein of the liver and superimpose the preoperative image 158 over the poor-quality live ultrasound image stream (intraoperative data 160) and display a holographic visualization within the field of view of the user. The holographic visualization includes a holographic representation of a tracked instrument 104 (e.g., interventional device) congruent with the registered holographic projection of the live ultrasound image stream (intraoperative data 160) and the holographic image of the hepatic vein derived from CT (preoperative data 158). This holographic visualization is used to navigate and guide the interventional device or tracked instrument 104 to the target anatomical structure.

It should be appreciated that there can be other situations where the preoperative data 158 will be displayed to the user, within the scope of this disclosure. In addition, it should be appreciated that one skilled in the art can select different surfaces and empty space to display the preoperative data 158, as desired.

Intraoperative data 160 can include information related to the patient and the anatomical site of the patient obtained in real-time, including during the medical procedure, for example, using the second holographic image acquisition system 110. For example, diagnostic medical procedures with respect to the preoperative data 158 can be performed simultaneously with the current medical procedure and collected and used in real time as intraoperative data 160. For example, a real time ultrasound image 156 can be obtained and integrated into the second holographic image acquisition system 110, which can provide a real time view, static or movable in real time, in conjunction with the second holographic image acquisition system 110. It should be appreciated that a skilled artisan can employ other information from other sources for the intraoperative data 160, as desired.

The intraoperative data 160 can be configured to provide the user with references during a medical procedure from that are obtained in real-time during the medical procedure. The augmented reality system 102 can display the intraoperative data 160 over the body of the patient. In addition, the augmented reality system 102 can align the projected intraoperative data 160, so it correlates and corresponds with the correct anatomical structure of the patient.

Referring to FIG. 7, the intraoperative data 160 can be super-imposed over the preoperative data 158 to identify changes that can occur between the preoperative imaging and the imaging occurring during the medical procedure. In addition, the intraoperative data 160 can be displayed when the intraoperative data 160 is better suited to be the navigational guide. For example, ultrasound imaging 156 can provide the most up-to-date imaging of the body of the patient. It should be appreciated that there can be other situations where the intraoperative data 160 will be displayed to the user, within the scope of this disclosure. In addition, it should be appreciated that the intraoperative data 160 can be projected on different surfaces and empty space.

In addition, the system 100 can correlate and establish relationships between the preoperative data 158 and the intraoperative data 160. For example, a hem line 168, shown in FIG. 7, permits for a measurement between a first end point 170 and a second end point 172. The first end 170 point is located within the ultrasound imaging 156 (intraoperative data 160) while the second end point 172 is located within the CT scan (preoperative data 158). Desirably, this permits the user to not only view the preoperative data 158 and the intraoperative data 160 simultaneously, but also perform diagnostic procedures using the materials from both data types.

Fused data 162 can include information, such as static images and recordings, that are generated by merging the preoperative data 158 and the intraoperative data 160. Desirably, the fused data 162 can present more concise and approximated images and animations to the user. It should be appreciated that fused data 162 can include other types of information, within the scope of this disclosure.

The fused data 162 can be configured to provide user with references during a medical procedure based on both the preoperative data 158 and the intraoperative data 160. In certain instances, the fusion of data can be performed in manual fashion. In other instances, the computer system 106 can be configured to generate the fused data 162 and transmit the plurality of operating information 154 to the augmented reality system 102, for example, using one or more algorithms set forth in the machine-readable instructions 130 or via artificial intelligence (AI). In some instances, this can be done through a wired connection. In other instances, this can be done wirelessly. It should be appreciated that the computer system 106 can transmit the plurality of operating information 154 using other methods and processes, within the scope of this disclosure.

The augmented reality system 102 can display the fused data 162 over the body of the patient. In addition, the augmented reality system 102 can align the projected fused data 162, so it correlates and corresponds with the correct anatomical structure of the patient. For example, as shown in FIG. 7, the augmented reality system 102 is displaying fused data 162 so that a CT scan (preoperative data 158) is super imposed over and aligned with the body of the patient, while the ultrasound imagining (intraoperative data 160) is imposed over the CT scan (preoperative data 158). In other instances, the fused data 162 simply displays the preoperative data 158 and the intraoperative data 160 simultaneously.

It should be appreciated that there can be other situations where the fused data 162 will be displayed to the user, within the scope of this disclosure. In addition, it should be appreciated that the fused data 162 can be projected on different surfaces and empty space.

Referring back to FIGS. 4a-4c, the system 100 for holographic augmented reality visualization and guidance includes an automatic segmentation and registration process 200. In particular, the automatic segmentation and registration process 200 can automatically split original preoperative scans (preoperative data 158) into segments and register each segment into the preoperative data 158. Desirably, the system 100 can then display each segment when needed, instead of the entire original preoperative scan.

With reference to FIG. 4a, the automatic segmentation and registration process 200 employs a CBCT imaging system 174 that includes a radiation source 176 and an image detector 178 located opposite the radiation source 176. The radiation source 176 emits a beam of X-rays 180 along a beam axis and toward an isocenter 182, thereby delivering radiation to a targeted volume 184 of a patient 186 interposed between the radiation source 176 and image detector 178. The image detector 178 receives the X-rays 180 that pass through the target volume 184 and generates preoperative CT scan images based on the X-rays 180 received. The CT scan images are used to generate a CBCT holographic representation (preoperative data 158) of the patients target anatomy.

In FIG. 4b, the preoperative CT scan images 158 are compared with the current position of the patient with the intraoperative data 160, e.g., ultrasound imaging 156 being super-imposed as a cone emitting from the ultrasound probe 188. The preoperative scans are automatically split into segments 190. Next, each segment is registered into the preoperative data 158. The segments 190 from the preoperative scans can create the training dataset to segment and register anatomy in real time. In one example. the automatic segmentation and registration process 200 can be accomplished using artificial intelligence (AI) and machine learning. In particular, the AI can include voxel-based segmentation and reconstruction from the training dataset. A specific threshold can be determined by an AI model to split imaging from preoperative data 158 into segments 190 that correspond with each anatomical structure in the imaging from the preoperative data 158. Anatomical structures and pathological states are identified from normal state through pattern recognition and adjustment of its features in its algorithm. In this way, these types of data processing can identify abnormal from normal anatomy based on voxel characterization. The automatic segmentation and registration process 200 can further obtain one or more intraoperative images 160 from the ultrasound imaging 156 being emitted from the ultrasound probe 188 and can co-register the intraoperative images 160 with the segments 190 into the preoperative data 158, thereby allowing the AI model to build a new segmented dataset.

With reference to FIG. 4c, by co-registering the preoperative segments (preoperative data 158) and the intraoperative images (intraoperative data 160), the preoperative data 158 and intraoperative data 160 can be merged together generating fused data 162 that provide the baseline for reconstructing the 3D representation 192, which can be projected as one or more holograms in the augmented reality system 102.

Referring back to FIG. 1, the computer system 106 can have a deformation engine 150 configured to align the preoperative data 158 with the corresponding anatomical structure within the body of the patient during the medical procedure. As previously discussed, the computer system 106 can be configured to selectively generate fused data 162 by merging the preoperative data 158 and the intraoperative data 160, identify deformation of the anatomical structure via differences between the preoperative data 158 and the intraoperative data 160, and transmit the fused data 162 to the augmented reality system 102. The deformation engine 150 allows for compensating for deformations of the anatomical structure in real-time, manually, or automatically through AI and machine learning. The deformation engine 150 can automatically compensate for the deformation of the anatomical structure by aligning the preoperative data 158 with the intraoperative data 160 through AI and machine learning. Furthermore, the deformation engine 150 manually compensates for the deformation of the anatomical structure by allowing the user to manually align the preoperative data 158 with the intraoperative data 160.

In particular, without the deformation engine 150, the preoperative data 158 can be misaligned with the corresponding anatomical structure due to the anatomical structures within the body of the patient deforming or shifting in positioning. The anatomical structures can deform or shift in positioning significantly from the time when the preoperative data 158 was collected. Desirably, the deformation engine 150 updates the positioning of the preoperative data 158, which can include segmented preoperative data 158 or unsegmented preoperative data 158, to align with the corresponding anatomical structure.

Referring to FIG. 6, in operation, the deformation engine 150 merges the coordinate systems of the preoperative data 158 and the intraoperative data 160. The deformation engine 150 also identifies and registers key anatomical structures 196 in the preoperative data 158 to be used as reference points 194. This can include identifying echogenic profiles of the anatomical structures manually or through AI. For example, the specific voxels associated with a tissue type can be identified and registered using AI and machine learning. The deformation engine 150 then identifies these reference points 194 in the intraoperative data 160 and compares the differences with the preoperative data 158. The differences between the intraoperative data 160 and the preoperative data 158 can include changes in the deformation and the spatial positioning of anatomical structures, represented as arrows in FIG. 6. However, it should be appreciated that a skilled artisan can identify other differences, within the scope of this disclosure.

Once differences have been identified, the deformation engine 150 can compensate for deformations by altering, deforming, or shifting the preoperative data 158 to align the preoperative data 158 to the corresponding anatomical structure 196. In some instances, the user can also manually alter, deform, or shift the preoperative data 158 to align the preoperative data 158 to the corresponding anatomical structure 196. For example, the deformation engine 150 allows the user to pull each reference point 194 identified on the anatomical structure profile 198 in the preoperative data 158 to align with the corresponding reference point 195 identified on the anatomical structure 196 in the intraoperative data 160. Desirably, this can refine the imagining of surrounding critical structures or the targeted pathway, which can result in improved accuracy during the medical procedure.

In some examples, the computer system 106 can also include a standard graphics and physics engine 152. The standard graphic and physics engines can set upper boundary conditions and lower boundary conditions on the preoperative data 158 based on the characteristics of the preoperative data 158 or anatomical structure. Advantageously, this can permit real time correction without substantially distorting the preoperative data 158. It should be appreciated that one skilled in the art can employ other graphic engines, physic engines, and simulations to manipulate the preoperative data 158, as desired.

A method 300 for holographic augmented reality visualization and guidance in performing a medical procedure is shown in FIG. 8. The method 300 includes a step 302 of providing the system 100. Then, at step 304, the preoperative data 158 can be selectively registered to the plurality of operating information. Next, at step 306, the intraoperative data 160 can be selectively registered to the plurality of operating information. Then, at step 308, the computer system 106 generates the fused data 162. As mentioned previously, the fused data 162 can be generated automatically or manually. Next, the preoperative data 158 can be selectively adjusted according to the deformation engine 150 where the preoperative data 158 does not align with the intraoperative data 160, at step 310. Then, at step 312, the computer system 106 transmits the plurality of operating information 154 to the augmented reality system 102. Next, the augmented reality system 102 selectively displays the intraoperative data 160 where the intraoperative data 160 permits the user to navigate the body of the patient, at step 314. Then, at step 316, the augmented reality system 102 selectively displays the preoperative data 158 where the intraoperative data 160 does not substantially permit the user to navigate the body of the patient. Next, the augmented reality system 102 selectively displays the fused data 162 where both the preoperative data 158 and the intraoperative data 160 permit the user to navigate the body of the patient, at step 318. Then, at step 320, the user can selectively adjust the plurality of operating information 154 in real-time.

Advantageously, the system 100 and methods 200, 300 can provide enhanced imaging for the user. In particular, the plurality of operating information, including the preoperative data 158, the intraoperative data 160 and the fused data 162, can provide enhanced imaging for the user. In addition, the deformation engine 150 can adjust for deformable anatomy.

While certain representative embodiments and details have been shown for purposes of illustrating the invention, it will be apparent to those skilled in the art that various changes can be made without departing from the scope of the disclosure, which is further described in the following appended claims.

What is claimed is:

1. A holographic augmented reality visualization and guidance system for performing a medical procedure on an anatomical structure of a subject by a user, comprising:

an augmented reality system configured to show a plurality of operating information to the user, the plurality of operating information including at least one of preoperative data of the anatomical structure, intraoperative data of the anatomical structure, and fused data of the anatomical structure; and a computer system in communication with the augmented reality system, the computer system having a deformation engine, the computer system including a graphics and physics engine configured to set an upper boundary condition and a lower boundary condition on the preoperative data based on a characteristic of the anatomical structure, wherein the computer system is configured to selectively generate the fused data by merging the preoperative data and the intraoperative data, identify deformation of the anatomical structure via a difference between the preoperative data and the intraoperative data, transmit the plurality of operating information including the fused data to the augmented reality system, and compensate for the deformation of the anatomical structure according to the deformation engine in real-time.

2. The system of claim 1, wherein the deformation engine automatically compensates for the deformation of the anatomical structure by aligning the preoperative data with the intraoperative data through artificial intelligence and machine learning before the computer system transmits the plurality of operating information to the augmented reality system.

3. The system of claim 1, wherein the deformation engine manually compensates for the deformation of the anatomical structure by allowing the user to manually align the preoperative data with the intraoperative data.

4. The system of claim 1, wherein the computer system generates the fused data by super-imposing the intraoperative data over the preoperative data.

5. The system of claim 1, wherein the computer system generates the fused data by super-imposing the preoperative data over the intraoperative data.

6. A method for holographic augmented reality visualization and guidance in performing a medical procedure on a patient by a user, the method comprising the steps of:

providing a system having an augmented reality system configured to display a plurality of operating information of the patient in an augmented reality environment, a first holographic image acquisition system, a second holographic image acquisition system, and a computer system having a deformation engine, the computer system further including a graphics and physics engine configured to set an upper boundary condition and a lower boundary condition on the preoperative data based on a characteristic of the preoperative data;

acquiring, by the first holographic image acquisition system, preoperative data from the patient;

acquiring, by the second holographic image acquisition system, intraoperative data from the patient;

selectively registering the preoperative data to the plurality of operating information;

selectively registering the intraoperative data to the plurality of operating information;

selectively generating, by the computer system, fused data;

selectively adjusting the preoperative data according to the deformation engine where the preoperative data does not align with the intraoperative data;

transmitting, by the computer system, the plurality of operating information to the augmented reality system;

selectively displaying, by the augmented reality system, the intraoperative data where the intraoperative data permits the user to navigate a body of a patient;

selectively displaying, by the augmented reality system, the preoperative data where the intraoperative data does not substantially permit the user to navigate the body of the patient;

selectively displaying, by the augmented reality system, the fused data where both the preoperative data and the intraoperative data permit the user to navigate the body of the patient; and selectively adjusting, by the user, the plurality of operating information in real-time.

7. The method of claim 6, wherein the first holographic image acquisition system is selected from a group consisting of a computerized tomography (CT) apparatus, cone beam computed tomography (CBCT) apparatus, a magnetic resonance imaging (MRI) apparatus, a projectional radiography apparatus, a positron emission tomography (PET) apparatus, a volumetric ultrasound and fluoroscopy system, and combinations thereof.

8. The method of claim 6, wherein the second holographic image acquisition system is selected from a group consisting of a general ultrasound, a transesophageal ultrasound, an endoscopic ultrasound, a point of care ultrasound, an ultrasound echocardiogram (ECG) imaging apparatus, a fluoroscopy apparatus, a transthoracic echocardiogram (TTE), a transesophageal echocardiogram (TEE), an intracardiac echocardiogram (ICE), and combinations thereof.

\* \* \* \* \*